US00PP24575P3

(12) United States Plant Patent
Egger

(10) Patent No.: US PP24,575 P3
(45) Date of Patent: Jun. 24, 2014

(54) ***HEUCHERA* PLANT NAMED 'PAPRIKA'**

(50) Latin Name: ***Heuchera* sp.**
Varietal Denomination: Paprika

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 144 days.

(21) Appl. No.: 13/507,972

(22) Filed: Aug. 10, 2012

(65) Prior Publication Data

US 2014/0047606 P1 Feb. 13, 2014

(51) Int. Cl.
*A01H 5/00* (2006.01)

(52) U.S. Cl.
USPC ..... Plt./440

(58) Field of Classification Search
CPC ..... A01H 5/00; A01H 5/12
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant characterized by spring leaves that are orange colored and veiled white, summer leaves are peach to burgundy colored and veiled white, a medium mounding habit, and good vigor.

2 Drawing Sheets

Botanical denomination: *Heuchera* sp.
Variety designation: 'Paprika'.

BACKGROUND OF THE INVENTION

The present invention relates to a new and distinct cultivar of *Heuchera* and given the cultivar name of 'Paprika'. *Heuchera* is in the family Saxifragaceae. *Heuchera* 'Paprika' came out of a planned breeding program to create a bright orange leaf *Heuchera*. This new cultivar originated from a cross between *Heuchera* K175-2, a proprietary non-commercial hybrid, as the seed parent, and *Heuchera* K232-2, a proprietary non-commercial hybrid, as, as the pollen parent.

Compared to the seed parent, *Heuchera* K175-2, the new cultivar has leaves that are orange to rose rather than rose to khaki colored.

Compared to the pollen parent, *Heuchera* K232-2, the new cultivar is more veiled and has leaves that are an orange to rose rather than peach colored.

Compared to *Heuchera* 'Vienna', U.S. Plant Pat. No. 23,308, the new cultivar has leaves that are less veiled and deep orange in spring and peach to burgundy in summer. The new cultivar has flowers that are very light pink rather than pink.

This new *Heuchera* is uniquely distinguished by:

1. spring leaves that are orange colored and veiled white,
2. summer leaves are peach to burgundy colored and veiled white,
3. a medium mounding habit, and
4. good vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a two-year-old plant of *Heuchera* 'Paprika' growing in a one gallon container outside in part sun in early May in Canby, Oreg.

FIG. 2 shows the same plant in July.

DETAILED PLANT DESCRIPTION

Figure 3:
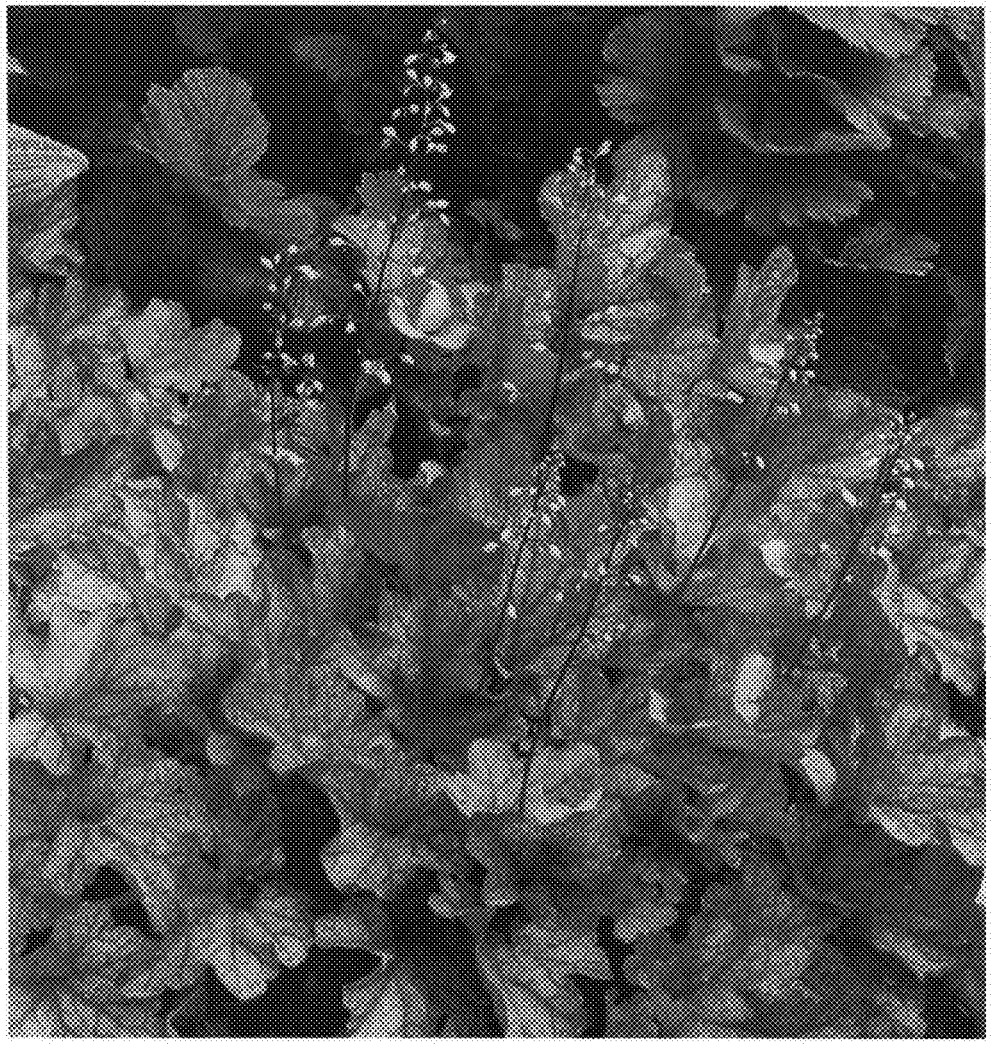
FIG. 3 shows the new cultivar in flower in the garden in September in Canby, Oreg.

The following is a detailed description of the new *Heuchera* cultivar based on observations of two-year-old specimens growing in one gallon containers in a cold greenhouse in March in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The *Royal Horticultural Society Colour Chart,* 2007 edition.

Plant:

*Form.*—Basal rosette, herbaceous perennial.
*Hardiness.*—USDA Zone 4 to 9.
*Size.*—17 cm tall from top of the foliage to the ground and 40 cm wide.
*Habit.*—Mounding.
*Vigor.*—Good.

Leaf:

*Type.*—Simple.
*Arrangement.*—Rosette.
*Shape.*—Broadly ovate.
*Number.*—About 50.
*Lobing/division.*—7 lobes, with shallow secondary lobes.
*Venation.*—Palmate.
*Margins.*—Crenate and lightly undulate.

*Apex*.—Mucronulate.
*Base*.—Cordate and overlapping.
*Blade size*.—Grows to 11 cm long and 10.5 cm wide.
*Surface texture*.—Glandular on top and bottom.
*Petiole description*.—Grows to 15 cm long and 3 mm wide, glandular hairs, Greyed Purple 187B.
*Leaf color*.—Color variable, topside depending on temperature and light conditions, spring leaves base color Orange Red 34B covered with veil interveinally, White NN155A; summer leaves to winter leaves Greyed Purple 185A with interveinal veil closest Red Purple 62A; bottom side Red Purple 59A in young leaves to Greyed Purple 185C in older leaves.

Inflorescence:
*Size*.—Grows to 5 cm wide and 14 cm long.
*Type*.—Thyrse.
*Number of flowers per thyrse*.—About 3.
*Number of thyrse*.—0 to 10, blooms sparingly, usually in late summer.
*Peduncle*.—Grows to 25 cm long, 3 mm wide at base, Greyed Purple 187B, glandular hairs, with 0 to 4 leaves (grow to 28 mm long and 27 mm wide, orbicular, 3 to 7 shallow lobes, crenate margins, mucronulate tip, base truncate, both sides glandular, Greyed Orange 174A on topside and Greyed Orange 178A on bottom; petiole to 5 mm long and 1 mm wide and Greyed Purple 187A).
*Pedicel*.—Variable in size, with glandular hairs, Greyed Purple 187B.
*Bloom period*.—Usually in late summer in Canby, Oreg.

Flower bud:
*Size*.—2.5 mm wide and 5 mm long.
*Description*.—Glandular puberulent, ovoid, down facing.
*Color*.—Greyed Purple 185D.

Flower:
*Type*.—Perfect.
*Shape*.—Campanulate.
*Size*.—7 mm long and 3.5 mm wide.
*Corolla description*.—5 petals, 2 mm long and 1.5 mm wide, narrowly spatulate, margins entire, tip acute, glabrous top and glandular on bottom, White NN155C.
*Calyx description*.—Campanulate, 6 mm long and 3.5 mm wide, with 5 lobes divided ⅓ way to the base, each 2 mm wide and 1.5 mm long, glandular hairs outside and glabrous inside, tips obtuse, margin entire; inside and out color Red Purple 69D on top ⅔ blending to Red Purple 65A on bottom ⅓.
*Stamen description*.—5 in number, filaments 3 mm long, White 155A, anthers 0.2 mm, Yellow Orange 23A, pollen Yellow Orange 23B.
*Pistil description*.—1, 2-beaked, 5 mm long and 2 mm wide; ovary 2 mm long and 2 mm wide, White 155A; style 2 mm long, White NN155A, stigma Greyed Purple 187C.
*Fragrance*.—None.
*Lastingness*.—Each thyrse blooms for about 3 weeks on the plant.

Fruit:
*Type*.—Two-beaked ovoid capsule.
*Fertility*.—Low.
*Size*.—4 mm long and 3 mm wide.
*Color*.—Greyed Brown 199C.

Seed:
*Shape*.—Linear.
*Size*.—2 mm long.
*Color*.—Black 202A.

Pest and disease tolerance: The new cultivar is typical to the genus. No known resistances to pests or diseases. No problems have been found in Canby, Oreg.

I claim:
1. A new and distinct *Heuchera* plant as herein illustrated and described.

* * * * *

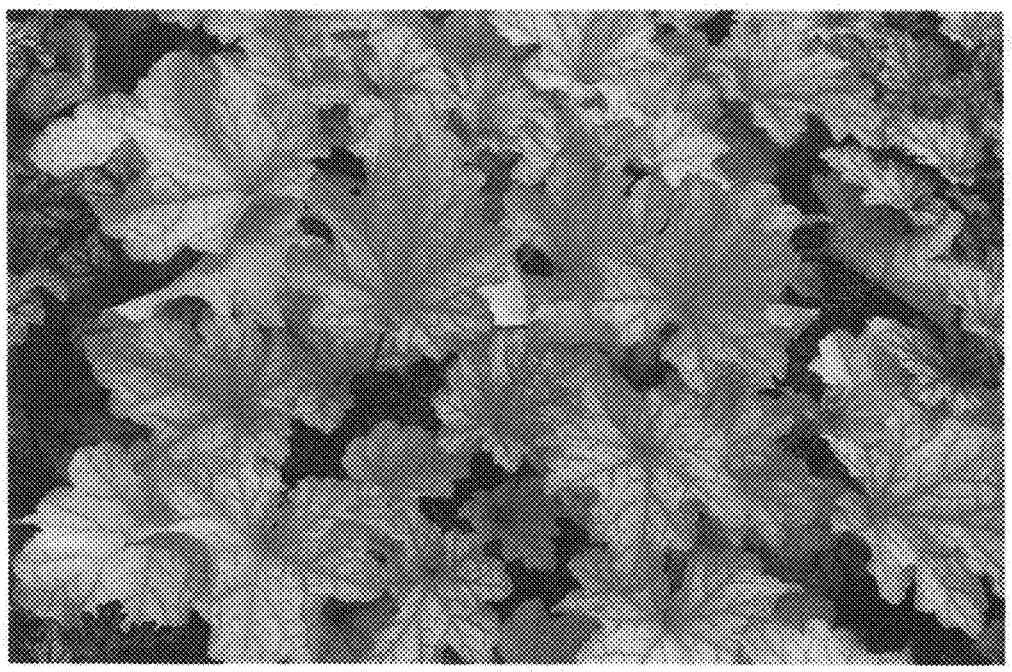
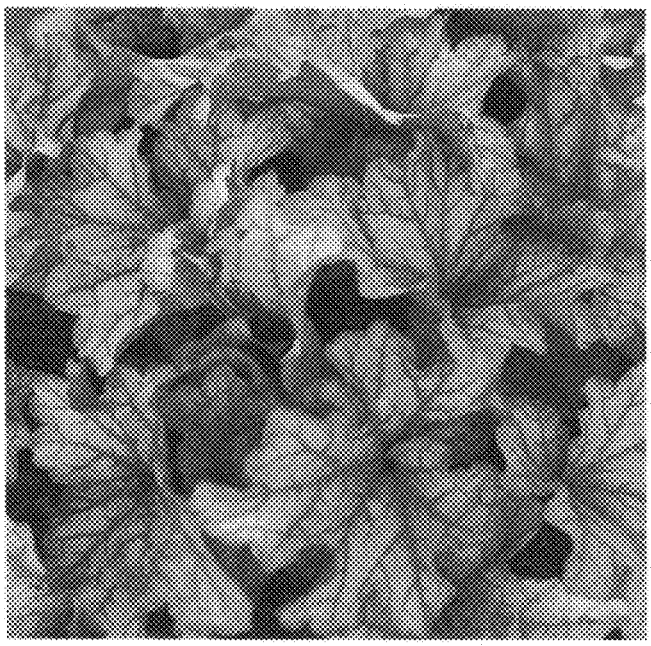
FIG. 1 above,
FIG.2 to left.